United States Patent [19]

Fisher

[11] Patent Number: 5,367,717

[45] Date of Patent: Nov. 29, 1994

[54] CUSPIDOR

[75] Inventor: William F. Fisher, Beavercreek, Oreg.

[73] Assignee: A-Dec, Inc., Newberg, Oreg.

[21] Appl. No.: 11,321

[22] Filed: Jan. 29, 1993

[51] Int. Cl.$^5$ ............................................. A61C 17/14
[52] U.S. Cl. .......................................... 4/263; 4/258; 4/262
[58] Field of Search .................. 4/258, 262, 263, 264, 4/265, 266, 420; 433/97, 33, 77, 79; 366/165, 174; D34/2

[56] References Cited

U.S. PATENT DOCUMENTS

| D. 258,007 | 1/1981 | Schmidt | D24/1 |
|---|---|---|---|
| 943,527 | 12/1909 | Escudel | 4/262 |
| 1,626,689 | 5/1927 | Pieper | 4/263 |
| 1,649,183 | 11/1927 | Pieper | 4/263 |
| 2,098,732 | 11/1937 | Prather | 433/32 |
| 2,098,932 | 11/1937 | Saffir | 4/263 |
| 2,371,597 | 3/1945 | Angell | 433/97 |
| 2,848,721 | 8/1958 | Fredrickson | |
| 3,229,368 | 1/1966 | Tocchini | 32/22 |
| 3,400,412 | 9/1968 | Turner | 251/62 |
| 3,613,131 | 10/1972 | Strom et al. | 4/263 |
| 3,650,033 | 3/1972 | Behne et al. | 32/22 |
| 3,718,974 | 3/1973 | Buchtel et al. | 32/22 |
| 3,771,226 | 11/1973 | Lieb et al. | 297/188 |
| 4,165,546 | 8/1979 | Philipson et al. | 4/262 |
| 4,307,475 | 12/1981 | Schmidt | 4/263 |
| 4,470,163 | 9/1984 | Kratochwilla | 4/263 |

FOREIGN PATENT DOCUMENTS

| 0097877 | 6/1983 | European Pat. Off. . | |
| 0526270 | 5/1955 | Italy . | |
| 99402 | 7/1940 | Sweden | 4/262 |
| 425658 | 3/1935 | United Kingdom | 4/263 |
| 939113 | 10/1963 | United Kingdom . | |
| 2045311 | 10/1980 | United Kingdom | 4/420 |

OTHER PUBLICATIONS

A-Dec "Century" two-page brochure circa Jan. 1978.
Takara Belmont 50-page Japanese language dental equipment catalog, cover and pp. 9-25, circa Jan. 1991.
Anthos "Teseo" six-page brochure circa Jan. 1992.
A-Dec 117-page equipment catalog, cover and pp. 31-38, Jan. 1991.
Signo "Grand" 19-page Japanese language brochure, cover, pp. 6, 17, circa Jan. 1991.
KaVo "Estetica® 1042 Ein Wichtiger Schritt in die Zukunft" German language 13-page brochure, pp. 1, 3, 10, circa Jan. 1991.
A-Dec 121-page catalog, cover and pp. 33-40, circa Sep. 1991.
A-Dec "J-Dec" two-page Japanese language brochure circa Jan. 1991.
Pelton and Crane one-page brochure circa Jan. 1991.
Robin Dental Company 40-pg. catalog, cover and p. 9, Feb. 1985.
Marcus Dental Equipment 15-page catalog, cover and p. 11, Mar. 1982.
Weber Dental Criterion-300, cover page only, Apr. 16, 1973.

(List continued on next page.)

Primary Examiner—Henry J. Recla
Assistant Examiner—Gregory M. Vidovich
Attorney, Agent, or Firm—Klarquist, Sparkman, Campbell, Leigh & Whinston

[57] ABSTRACT

A cuspidor having a substantially rounded basin with a bottom, a substantially upright surrounding sidewall and a fluid inlet spaced above the bottom adjacent one end of the basin for directing flushing fluid into the basin. The juncture between the bottom and sidewall of the basin is formed in a concave curve which varies from a first radius at the end of the basin adjacent the fluid inlet to a smaller second radius adjacent the opposite end of the basin. The bottom also has a substantially flat section adjacent a portion of the juncture section which merges with an intermediate section for directing flushing fluids to a drain hole. The configuration of the basin provides efficient flushing and minimizes the possibility of flushing fluid splashing over the sidewall.

19 Claims, 2 Drawing Sheets

OTHER PUBLICATIONS

Osada "FX Series" 31-page Japanese language brochure, cover and pp. 1, 17, 28, circa Jan. 1991.

A-Dec two-page compilation of holder devices: 1969, 1974, 1976, 1980, 1987, 1991, circa Jan. 1991.

Dentech 32-page catalog, cover and pp. 2-18, circa Jan. 1991.

Ampco Dental Products four-page brochure, cover page, circa Jan. 1991.

Engle "ME-2" two-page brochure circa Jan. 1991.

Pelton & Crane "Spirit" two-page brochure Jan., 1984.

Takara Belmont 36-page Japanese language brochure, cover and pp. 3, 16-22, circa Jan. 1991.

Siemens 27-page catalog, cover and pp. 2-3, 6-7, 17, Feb. 1991.

KaVo "Systematica® 1060" four-page French language brochure, circa Jan. 1991.

J. Morita Corporation "Surpass" 21-page Japanese language brochure, cover and pp. 7-8, 15, 18, circa Jan. 1991.

Belmont "SP-Six" ten-page brochure, pp. 7, 10, Aug., 1985.

S-T Products "Performers" six-page brochure, Jul. 1983.

Elan 2000 III 20-page Japanese language catalog, cover and pp. 13, 19, circa Jan. 1991.

Dentrex "Delivery System" four-page brochure circa Jan. 1991.

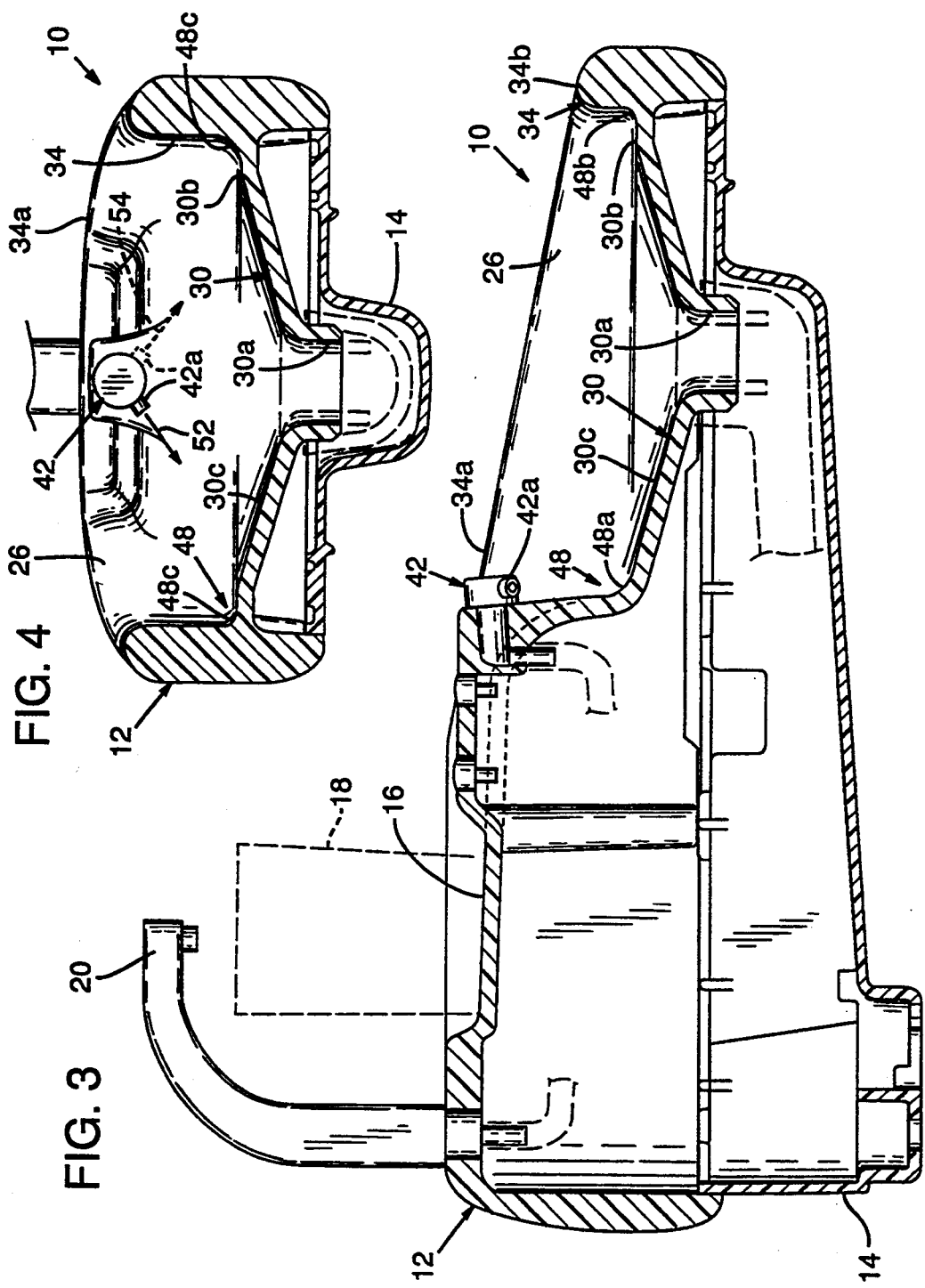

CUSPIDOR

FIELD OF THE INVENTION

This invention relates to a cuspidor, and more particularly to such a cuspidor as would be used in a dental office.

Background of the Invention

Cuspidors into which a patient can spit having fluid flushing systems have been known for some time. In the past these often included a substantially circular bowl with an inturned upper lip and a water jet directed about the periphery of the underside of the inturned lip to sweep around the bowl and exit through a central drain hole in the bottom of the bowl.

More recently newer styles of cuspidors are being designed with substantially upright sidewalls lacking the inturned upper lip which previously confined water in the basin. Further, governmental restrictions now require that the system be such that no fluid from the basin can be syphoned back into the fluid supply if there is a drop in pressure in the fluid supply. One way of accomplishing this is to assure that the flushing fluid inlet be at a higher elevation than the maximum height of a quantity of water that could be held in the basin. Both of these design revisions have resulted in cuspidors which may have insufficient control of flushing fluids dispensed into the basin to prevent the fluid from splashing over the top of the basin sidewall during a flushing procedure.

A general object of the present invention is to provide a novel cuspidor having a rounded basin with substantially upright sidewalls with a fluid inlet for directing fluid into the basin and the design of the basin is such as to inhibit splashing of fluids over the top of the sidewalls during flushing operation.

Another object of the present invention is to provide a novel cuspidor wherein the top of the sidewall slopes downwardly from one end to the opposite end, the fluid inlet is disposed adjacent the higher end and above the level of the lower end, and the contour of the basin of the cuspidor is formed to inhibit splashing of flushing fluid over the top of the lower end.

More specifically, an object of the present invention is to provide such a cuspidor which has a bottom and in which the juncture between the bottom and the substantially upright sidewalls of the basin are formed in a convex curve which has a first radius adjacent the end of the basin into which the fluid inlet directs flushing fluids, and at the opposite end of the basin has a second radius which is less than the first radius.

A still further object of the invention is to provide such a novel cuspidor in which the juncture curve blends in a smooth transition from the first radius to the second radius in a region between opposite ends of the basin.

Yet another object of the invention is to provide a novel cuspidor which is easily and inexpensively manufactured with known molding techniques.

A still further object of the present invention is to provide such a novel cuspidor in which the bottom of the basin includes a substantially flat section adjacent a portion of the juncture between the bottom and upright sidewalls, and an intermediate section that slopes downwardly from the flat section and juncture section to a drain hole intermediate opposite ends of the basin.

These and other objects and advantages will become more fully apparent as the following description is read in conjunction with the drawings.

BRIEF DESCRIPTION OF THE DRAWINGS

FIG. 3 is an enlarged cross-sectional view taken generally along the line 3—3 in FIG. 2; and FIG. 4 is an enlarged cross-sectional view taken generally along the line 4—4 in FIG. 2.

DETAILED DESCRIPTION OF A PREFERRED EMBODIMENT

Figure 1:
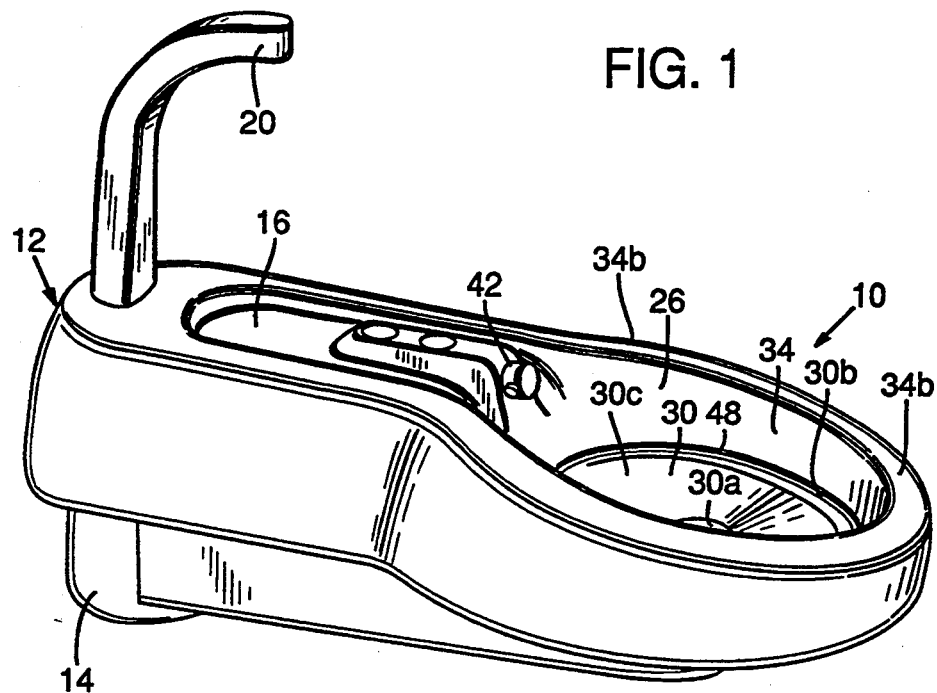
FIG. 1 is a perspective view of a cuspidor constructed according to an embodiment of the invention.
Figure 2:
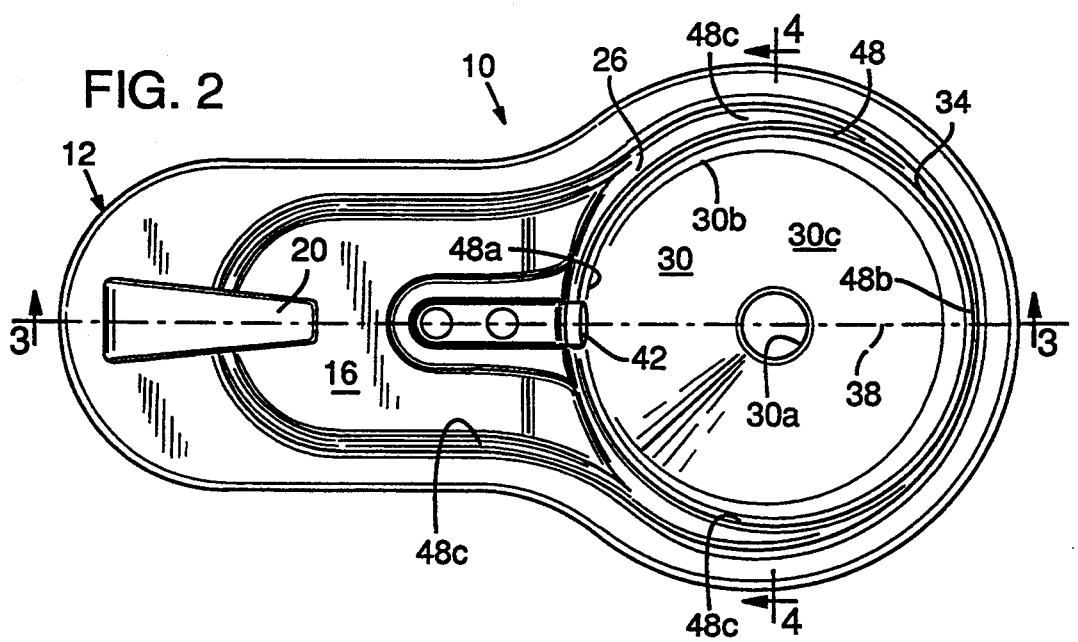
FIG. 2 is a top plan view of the cuspidor illustrated in FIG. 1.

Referring to the drawings, and first more particularly to FIG. 1, at 10 is indicated generally a cuspidor constructed according to a preferred embodiment of the invention. The cuspidor includes a formed upper body section 12 to which is secured a formed under body section 14.

The upper body section includes a depression 16 in which a glass, such as that illustrated at 18 in dashed outline in FIG. 3, may be supported. An upright spout 20 is operable to fill the glass with water.

Situated forwardly of depression 16 is a rounded basin 26 having a bottom 30 and a surrounding substantially upright sidewall 34.

The cuspidor 10 is substantially symmetrical about a longitudinal centerline 38 and thus a description of structure associated with one side of the cuspidor will relate also to the opposite side of the cuspidor.

As is best seen in FIGS. 1 and 3, the top of one end of sidewall 34, indicated here at 34a, is higher than the top of the sidewall at the opposite, or outer, end 34b. The top of the sidewall of the basin slopes gradually downwardly from end 34a to 34b. The upper marginal edge portions of the sidewall are substantially rounded, as seen in the cross sections of FIGS. 3 and 4 to provide ease of molding and a pleasing finished design.

A fluid inlet 42 is mounted at end 34a of the basin at an elevation higher than the top of end 34b. Fluid inlet 42 has a nozzle 42a which can be shifted either to a first position as seen in solid outline in FIG. 4 to direct flushing fluid to the left in FIG. 4, or to the opposite side as shown in dashed outline.

The fluid inlet is positioned above the elevation of the top of sidewall portion 34b to meet governmental anti-syphoning requirements. Explaining further, governmental regulations require that a water system be set up so that fluids will not be drawn back into the system if there is a substantial drop in pressure. One way to accomplish this is to construct the basin with its outer end wall 34b lower than the fluid inlet 42 to assure that any body of fluids which may collect in the basin would never rise above the height of top wall 34b, and thus remain substantially below the level of the inlet 42.

Referring again to FIGS. 3 and 4, it will be seen that bottom 30 of the basin includes three sections. First, is a substantially centrally disposed drain hole 30a intermediate opposite ends of the basin. An outer portion of the bottom is formed by a substantially flat section 30b as will be described in greater detail below. Extending between flat section 30b and drain hole 30a is an intermediate section 30c which slopes downwardly to drain hole 30a.

Bottom 30 and upright sidewall 34 are connected by a juncture section 48 extending from the bottom to the sidewall in the shape of a concave curve. The concave curve of the juncture section has a first radius portion 48a adjacent the end of the basin supporting the inlet faucet, and a second radius portion 48b adjacent the opposite, or outer, end of the basin. Portion 48b has a radius substantially less than the radius of portion 48a. In a preferred embodiment, the radius of portion 48b is approximately one-half of the radius of portion 48a.

In the illustrated embodiment the basin has an inner diameter of approximately seven inches and a bowl height of approximately 0.85 inches from the flat bottom section 30b to the top of wall portion 34b. The radius of curvature of portion 48a would be in a range of 0.4 to 0.6 inch and at portion 48b in a range of 0.2 to 0.3 inch. Radii 48a, 48b, are approximately 0.5 inch and 0.25 inch, respectively, in the illustrated embodiment.

The concave curve of the juncture section blends in a substantially smooth transition from the first radius 48a to the second radius 48b in a region of the basin between these opposite ends of the bowl. Such transition curves are disposed at opposite sides of the basin in regions indicated generally at 48c. The transition may occur over a length of approximately two inches.

Flat section 30b extends only partially about the basin. It begins a distance to one side of centerline 38, emanating from first radius section 48a, and increases gradually to a maximum width adjacent second radius section 48b. Its maximum width is the difference between the dimensions of the first radius 48a and second radius 48b. In the illustrated embodiment this width would be about 0.25 inch.

In operation, when it is desired to flush materials from the basin a valve (not shown) is actuated to cause flushing fluid (water) to jet from fluid inlet 42 in the direction of arrow 52, i.e., somewhat downwardly and toward one side of the basin. The flushing fluid sweeps downwardly and around the inside of the upright sidewall 34 of the basin and may be somewhat retained at a selected elevation by flat section 30b of the bottom and juncture section 48 between the sidewall and basin bottom. If the juncture section radius were to remain at the larger radius of section 48a, by the time the flushing fluid reached lower sidewall portion 34b it might have a tendency to ride up and over the top wall, thus causing it to splash out of the basin. For this reason, the juncture section radius transitions from the larger radius curvature at 48a to the smaller radius curvature of 48b. It has been found that by providing this transition to a smaller radius juncture section, splashing of flushing fluids over the outer end sidewall is inhibited.

The fluid moves in a generally circular path about the basin and is drawn by gravity downwardly to intermediate section 30c and then out through drain hole 30.

As seen in dotted outline in FIG. 4, the fluid inlet 42a may be turned to direct a stream of flushing fluid in the direction of arrow 54 to produce a flow of flushing fluid to the opposite side of the basin, as previously described. Since the basin is symmetrical about its centerline, the same operation as previously described occurs. With this variability in the direction of flushing fluid flow the basin may be placed on either side of a patient who may need to spit into the cuspidor and have materials flushed from the basin.

Although a preferred embodiment of the invention has been described herein, it should be recognized that variations and modifications are possible without departing from the spirit of the invention as set out in the following claims.

I claim:

1. A cuspidor comprising a rounded basin including a bottom and a substantially upright surrounding sidewall having a top, a fluid inlet spaced above the bottom adjacent one end of the basin for directing flushing fluid into the basin, and a juncture section interconnecting the bottom and sidewall of the basin, said juncture section being formed in a concave curve extending from the bottom to the sidewall which has a first radius adjacent said one end of the basin and at the opposite end of the basin has a second radius which is less than said first radius, and the top of the sidewall adjacent said opposite end of the basin is lower than said fluid inlet.

2. The cuspidor of claim 1, wherein said concave curve blends in a smooth transition from said first radius to said second radius in a region of the basin between said one end and said opposite end.

3. The cuspidor of claim 2, wherein the basin is substantially symmetrical on opposite sides of a center line extending from said one end to said opposite end of the basin and said concave curve blends in a smooth transition from said first radius to said second radius in opposed side regions of the basin between said one end and said opposite end.

4. The cuspidor of claim 3, wherein said fluid inlet is selectively variable to direct fluid flow either toward one side of the basin or the opposite side.

5. The cuspidor of claim 1, wherein the top of said sidewall slopes downwardly on progressing from said one end toward said opposite end.

6. The cuspidor of claim 1, wherein said bottom comprises a drain hole intermediate opposite ends of the basin, a substantially flat section adjacent a portion of said juncture section adjacent said opposite end, and an intermediate section which slopes downwardly from said flat section and a remaining portion of said juncture section adjacent said one end.

7. The cuspidor of claim 6, wherein said flat section has a width substantially equal to the difference between said first radius and said second radius.

8. The cuspidor of claim 1, wherein said second radius is approximately one half said first radius.

9. The cuspidor of claim 1 wherein said first radius is in a range of 0.4 to 0.6 inch and said second radius is in a range of 0.2 to 0.3 inch.

10. A cuspidor comprising a rounded basin having a bottom and a substantially upright surrounding sidewall, a fluid inlet spaced above the bottom adjacent one end of the basin for directing flushing fluid into the basin, a junction section interconnecting the bottom and sidewall of the basin, said juncture section being formed in a concave curve extending from the bottom to the sidewall which has a first radius adjacent said one end of the basin and at an opposite end of the basin has a second radius which is less than said first radius, said concave curve blending in a smooth transition from said first radius to said second radius in a region of the basin between said one end and said opposite end, and said drain hole has a drain hole intermediate said one end and said opposite end of the basin, a substantially flat section adjacent a portion of said juncture section adjacent said opposite end, and an intermediate section which slopes downwardly to said drain hole from said flat section and a remaining portion of said juncture section adjacent said one end.

11. The cuspidor of claim 10, wherein the basin is substantially symmetrical on opposite sides of a center line extending from said one end to said opposite end of the basin and said concave curve blends in a smooth transition from said first radius to said second radius in opposed side regions of the basin between said one end and said opposite end.

12. The cuspidor of claim 10, where said sidewall has a top and the top of the sidewall at said opposite end is lower than said fluid inlet.

13. The cuspidor of claim 12, wherein the top of said sidewall slopes downwardly on progressing from said one end toward said opposite end.

14. The cuspidor of claim 10, wherein said second radius is approximately one half said first radius.

15. The cuspidor of claim 10, wherein said first radius is in a range of 0.4 to 0.6 inch and said second radius is in a range of 0.2 to 0.3 inch.

16. A cuspidor comprising a rounded basin having a bottom and a substantially upright surrounding sidewall which is higher at one end of the basin than at the opposite end said sidewall having a top which slopes downwardly on progressing from said one end toward said opposite end, a fluid inlet adjacent said one end of the basin spaced above an elevation of said opposite end of the sidewall for directing flushing fluid into the basin, and a juncture section interconnecting the bottom and sidewall of the basin formed in a concave curve extending from the bottom to the sidewall which has a first radius adjacent said one end of the basin and at the opposite end of the basin has a second radius which is less than said first radius and said concave curve blends in a smooth transition from said first radius to said second radius in a region between said one end and said opposite end.

17. The cuspidor of claim 16, wherein the basin is substantially symmetrical on opposite sides of a center line extending from said one end to said opposite end of the basin and said concave curve blends in a smooth transition from said first radius to said second radius in opposed side regions of the basin between said one end and said opposite end.

18. The cuspidor of claim 16, wherein said second radius is approximately one half said first radius.

19. The cuspidor of claim 16, wherein said bottom comprises a drain hole intermediate opposite ends of the basin, a substantially flat section adjacent said juncture section adjacent said opposite end, and an intermediate section which slopes downwardly to said drain hole from said flat section and a remaining portion of said juncture section adjacent said one end.

* * * * *